United States Patent [19]

Tepic

[11] Patent Number: 5,051,482

[45] Date of Patent: Sep. 24, 1991

[54] METHOD AND APPARATUS FOR PREPARING A SELF-CURING TWO-COMPONENT POWDER LIQUID BONE CEMENT

[75] Inventor: Slobodan Tepic, Davos, Switzerland

[73] Assignee: Laboratorium für experimentelle Chirurgie, Davos, Switzerland

[21] Appl. No.: 251,209

[22] PCT Filed: Nov. 19, 1986

[86] PCT No.: PCT/EP86/00669

§ 371 Date: Jun. 23, 1988

§ 102(e) Date: Jun. 23, 1988

[87] PCT Pub. No.: WO88/03811

PCT Pub. Date: Jun. 2, 1988

[51] Int. Cl.$^5$ .................... C08F 265/06; A61M 5/32; A61B 19/00

[52] U.S. Cl. .................... 525/309; 525/265; 604/416; 222/386.5; 222/80

[58] Field of Search ............... 525/309, 265; 604/416; 222/386.5, 80

[56] References Cited

U.S. PATENT DOCUMENTS 3,739,947  6/1973  Baumann et al. .................... 604/416
4,463,875  8/1984  Tepic .................... 222/82
4,490,497  12/1984  Evrard et al. .................... 525/309
4,808,184  2/1989  Tepic .................... 604/56

Primary Examiner—John C. Bleutge
Assistant Examiner—Vasu S. Jagannathan
Attorney, Agent, or Firm—Walter C. Farley

[57] ABSTRACT

The method of preparing a self-curing two-component powder liquid bone cement comprising a powder component consisting of polymethylmethacrylate (PMMA) particles (1) containing benzoyl peroxide (BPO) as a polymerization catalyst (2), and methylmethacrylate (MMA) as a liquid polymerizable component (3), is performed by the following two steps: A) an evacuated, inflexible chamber (4) of a syringe (11) is filled essentially completely with the PMMA particles (1) which are at least partially solvable in the MMA monomer (3) and containing the BPO (2) distributed throughout the PMMA particles (1); B) by the action of the vacuum in the interspaces between the PMMA particles (1) the said interspaces are essentially completely flooded and the said PMMA particles are completely wetted by the said MMA monomer (3) and thereby at least a surface layer (9) of said PMMA particles (1) is dissolved and the corresponding BPO (2) contained in the said dissolved surface layer (9) initiates the polymerization process in the flooded cement mixture (7).

11 Claims, 6 Drawing Sheets

METHOD AND APPARATUS FOR PREPARING A SELF-CURING TWO-COMPONENT POWDER LIQUID BONE CEMENT

BACKGROUND OF THE INVENTION

This invention relates to a method of preparing a self-curing two-component powder liquid bone cement comprising a powder component consisting of particles containing a polymerization catalyst, and a liquid component containing a polymerizable monomer, prepolymer or mixtures thereof.

Various proposals have been made for mixing bone cement under vacuum, but mostly for avoiding inhalation of the toxic monomer vapours developing during preparation of bone cement. No utilizable cement mixture is obtained with all these known methods unless the powder and liquid components are not mechanically stirred and homogenized.

It is known, however, that such mechanical stirring, even under vacuum, produces air inclusions which weaken the finally hardened cement mass. Furthermore the accuracy of the powder liquid ratio cannot be guaranteed with the known methods of bone cement mixing since errors of the operator are always possible.

In the pending but not prepublished International Patent Application No. PCT/EP 85/00227 a method for mixing bone cement under vacuum according to the preamble of claim 1 of the present invention is described which uses normal polymethylmethacrylate (PMMA) beads coated with benzoyl peroxide (BPO) as a polymerization catalyst. Whereas this method overcomes the most essential drawbacks of commercially available bone cements, namely poor mixing, high exotherm and creation of porosities, its disadvantage lies in the fact that the BPO deposited on the surface of the PMMA-beads is quickly washed away when the evacuated powder component is flooded with the liquid component (methylmethacrylate) producing an inhomogeneous gradiant in the BPO concentration and thereby an irregular polymerization process.

SUMMARY OF THE INVENTION

The invention as claimed is intended to remedy these drawbacks. It solves the problem of how to design a method for preparing a bone cement without manual or mechanical mixing exhibiting a regular course of polymerization and a homogeneous structure of the hardened cement with practically no porosities.

The advantages offered by the invention are mainly the ease of handling, the quick and reliable mixing, the prevention of high exotherm and of porosities and the significantly improved physical values of the bone cement obtained by the method according to the invention.

The various features of novelty which characterize the invention are pointed out with particularity in the claims annexed to and forming part of this disclosure. For the better understanding of the invention, its operating advantages and specific objects attained by its use, reference should be had to the accompanying drawings and descriptive matter in which are illustrated and described preferred embodiments of the invention.

DESCRIPTION OF THE PREFERRED EMBODIMENTS

The basic method according to this invention consist of flooding polymethylmethacrylate (PMMA) beads confined in an inflexible, at least partially evacuated tubular chamber 4 of a syringe 11 with liquid methylmethacrylate, thereby obtaining a self-curing cement mixture without the need of manual or mechanical mixing.

The chemical composition of the main components and of the usual additives (powder, liquid, polymerization catalyst, polymerization activator, radio-opaquer, stabilizer, antibiotics) used in the method according to the invention is similar to that known from commercially available bone cements, with the exception of the PMMA beads.

Figure 1:
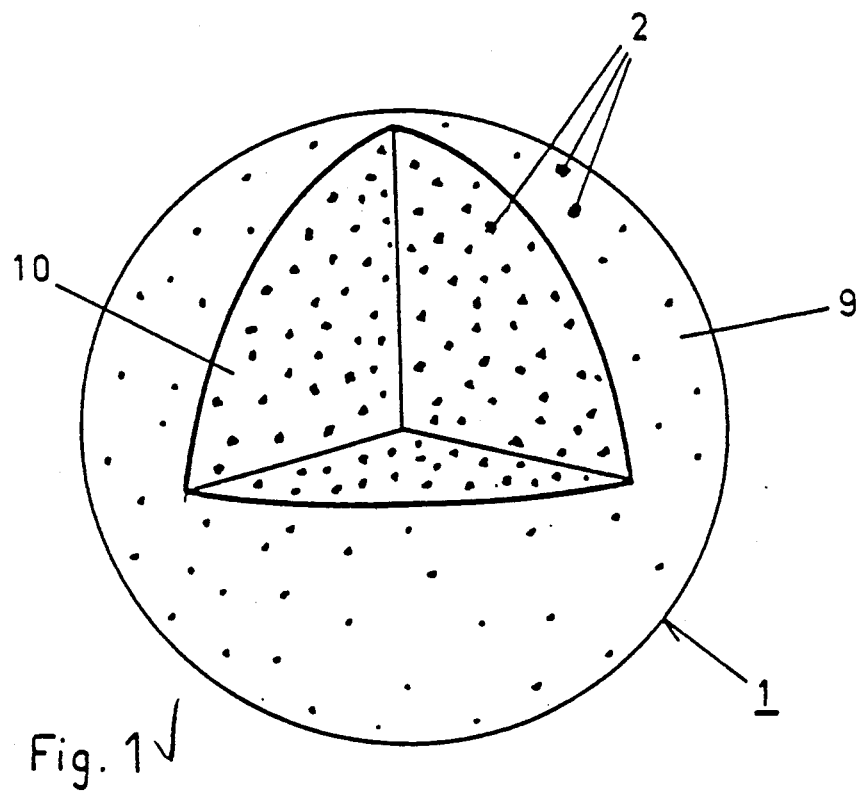
FIG. 1 is a perspective view of a powder particle used in the method according to the invention.
Figure 2:
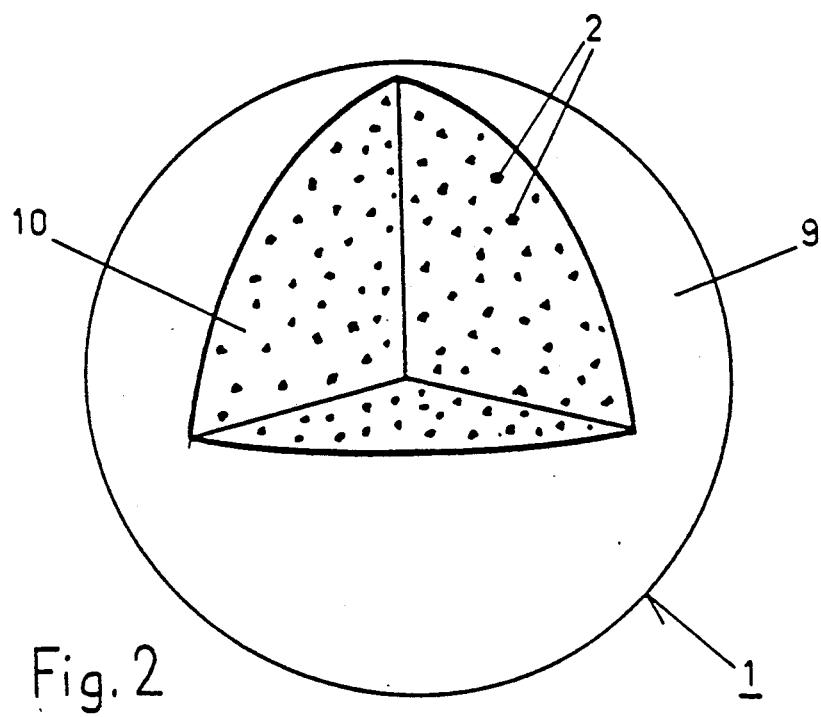
FIG. 2 is a perspective view of a specially manufactured powder particle used in the method according to the invention.
Figure 3:
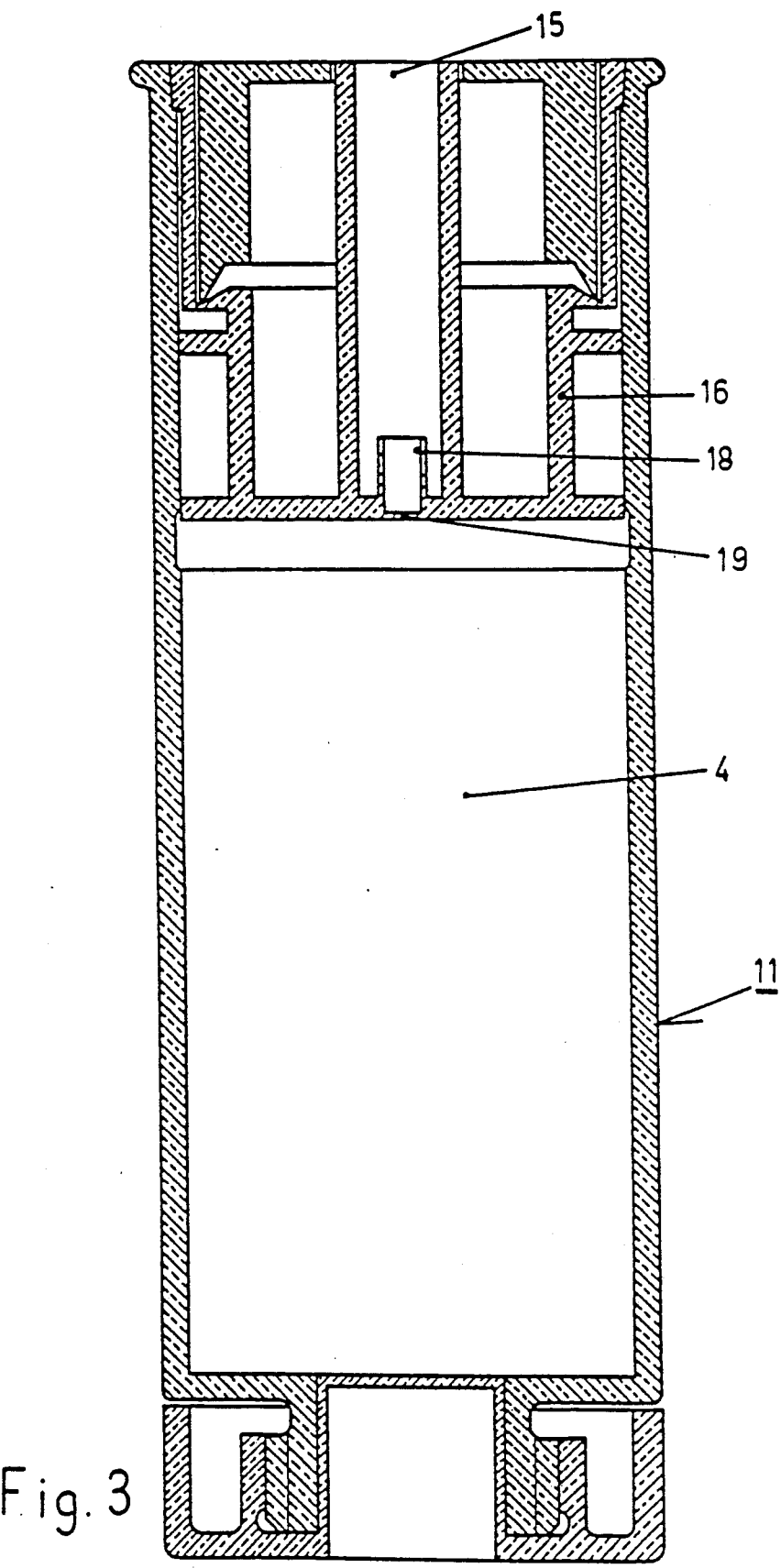
FIG. 3 is a sectional view of the empty syringe used for carrying out the method according to the invention.
Figure 4:
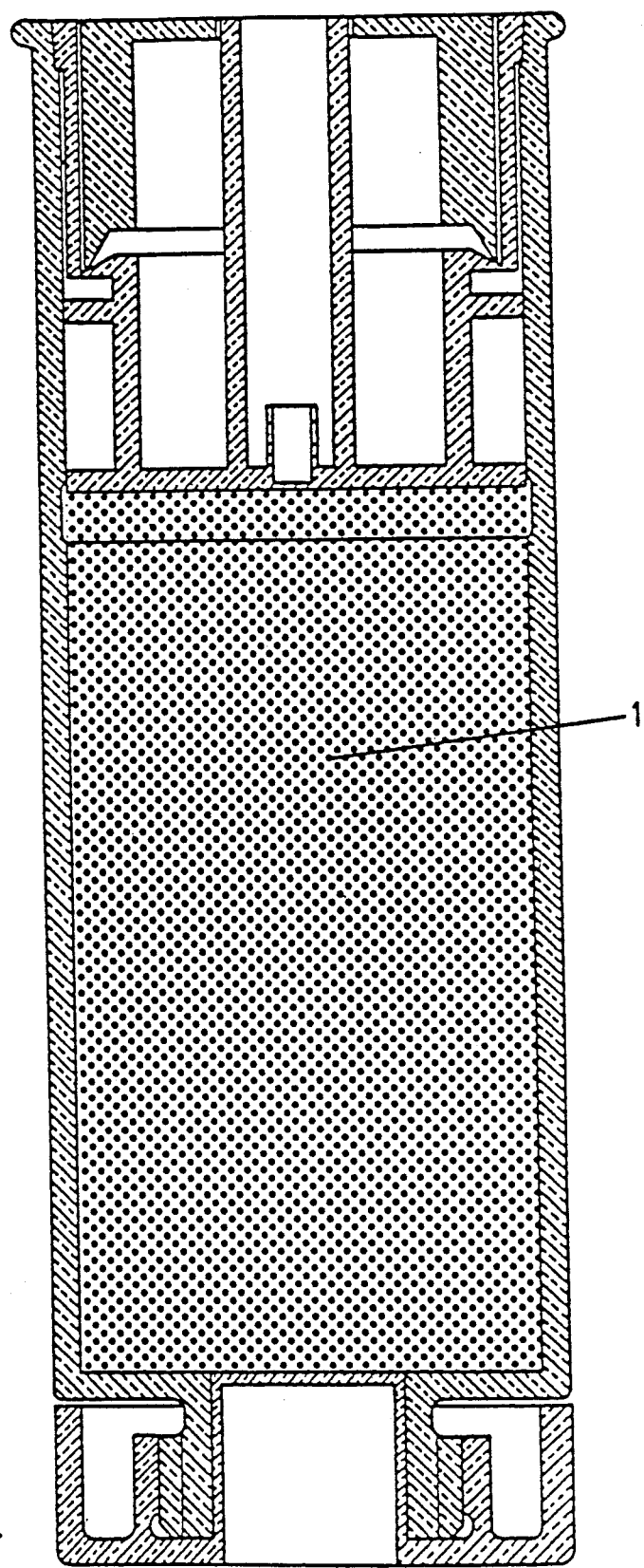
FIG. 4 is a sectional view of the filled syringe used for carrying out the method according to the invention.

Said PMMA beads 1 as shown in FIG. 1 contain benzoylperoxide (BPO) particles 2 acting as the polymerization catalyst which are distributed in almost uniformly throughout the PMMA beads 1, i.e. the BPO concentration within the surface layer 9 and in the interior 10 of said beads 1 is approximately the same. Although PMMA beads as shown in FIG. 1 are usable for the method according to the invention a similar "surface washing" effect, though less pronounced as commented in the prior art description above is observed. In order to achieve a more perfect homogeneity of the BPO throughout the flooded cement mixture the PMMA beads shown in FIG. 1 are subjected to a pretreatment which consists of washing them with water, thereby obtaining an almost complete removal of BPO from the surface layer 9 of said beads 1. The result of this pretreatment is shown in FIG. 2. Furthermore a very smooth surface of said PMMA beads 1 is obtained which contributes significantly to an enhanced flooding of said PMMA beads 1 by the liquid methylmethacrylate (MMA).

For a better understanding of the single steps involved in the preparation of the bone cement according to the invention the procedure is described in more detail reference being made to FIGS. 2 to 7.

The flooding of said PMMA beads 1 is effected by the action of the vacuum in the interspaces between the PMMA beads 1. To this effect an ampoule 12 with the liquid MMA monomer 3 is opened and inserted into an adapter 13. The needle 14 of said adapter 13 is inserted into the bore 15 of the piston 16. The tip 17 of the needle 14 is seated into the seal 18 of said piston 16 and cuts the diaphragm 19 of said piston 16. Monomer 3 is sucked into said chamber 4 by the action of the vacuum as shown by arrows 21 in FIG. 5.

Figure 7:
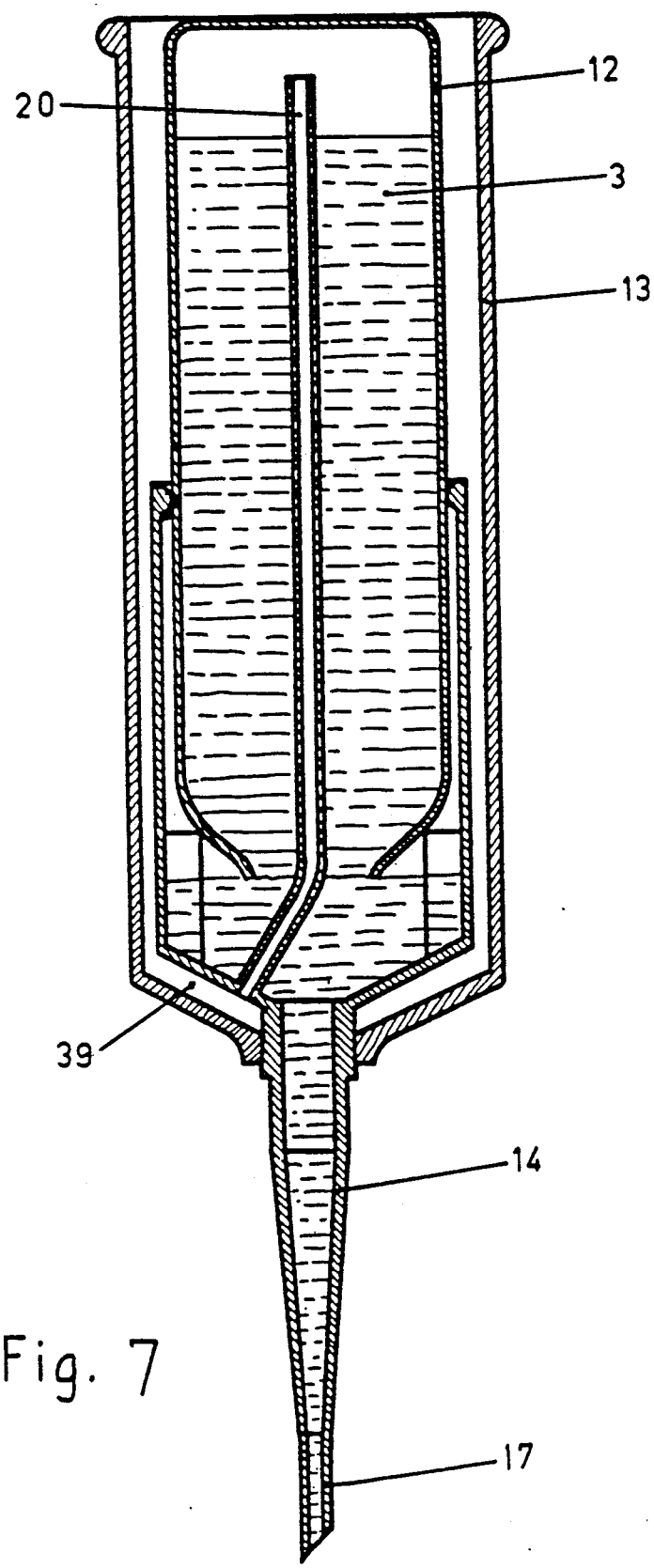
FIG. 7 is a sectional view of the ampoule and the adapter used for introducing the liquid component.

As can be seen from FIG. 7 the vent tube 20 of said adapter 13 allows for pressure compensation in said ampule 12. Said vent tube 20 is connected to a reservoir 39 which prevents flowing out of any liquid monomer 3 through said vent tube 20.

Figure 5J:
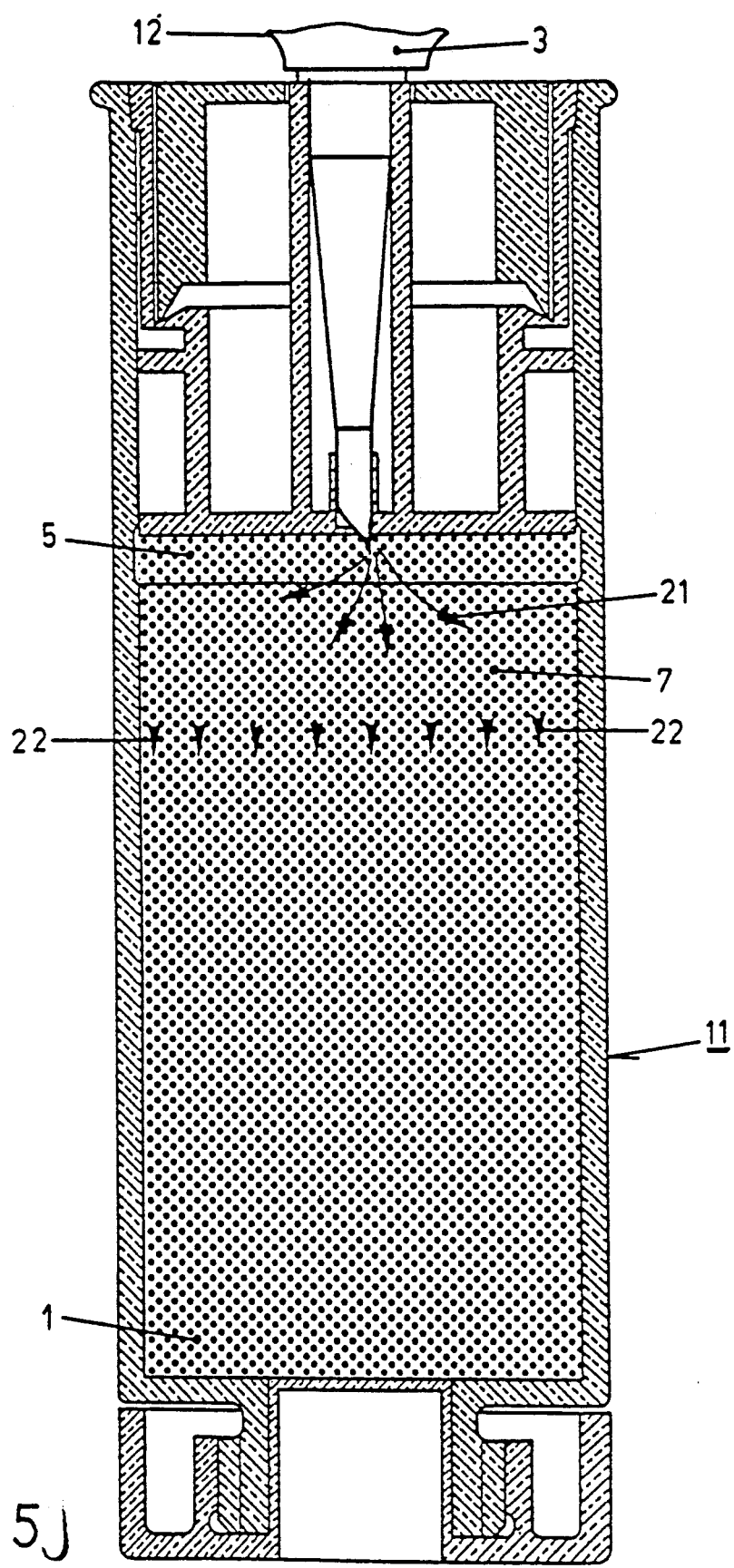
FIG. 5 is a sectional view of the syringe according to FIG. 4 with the inserted adapter according to FIG. 7.
Figure 6:
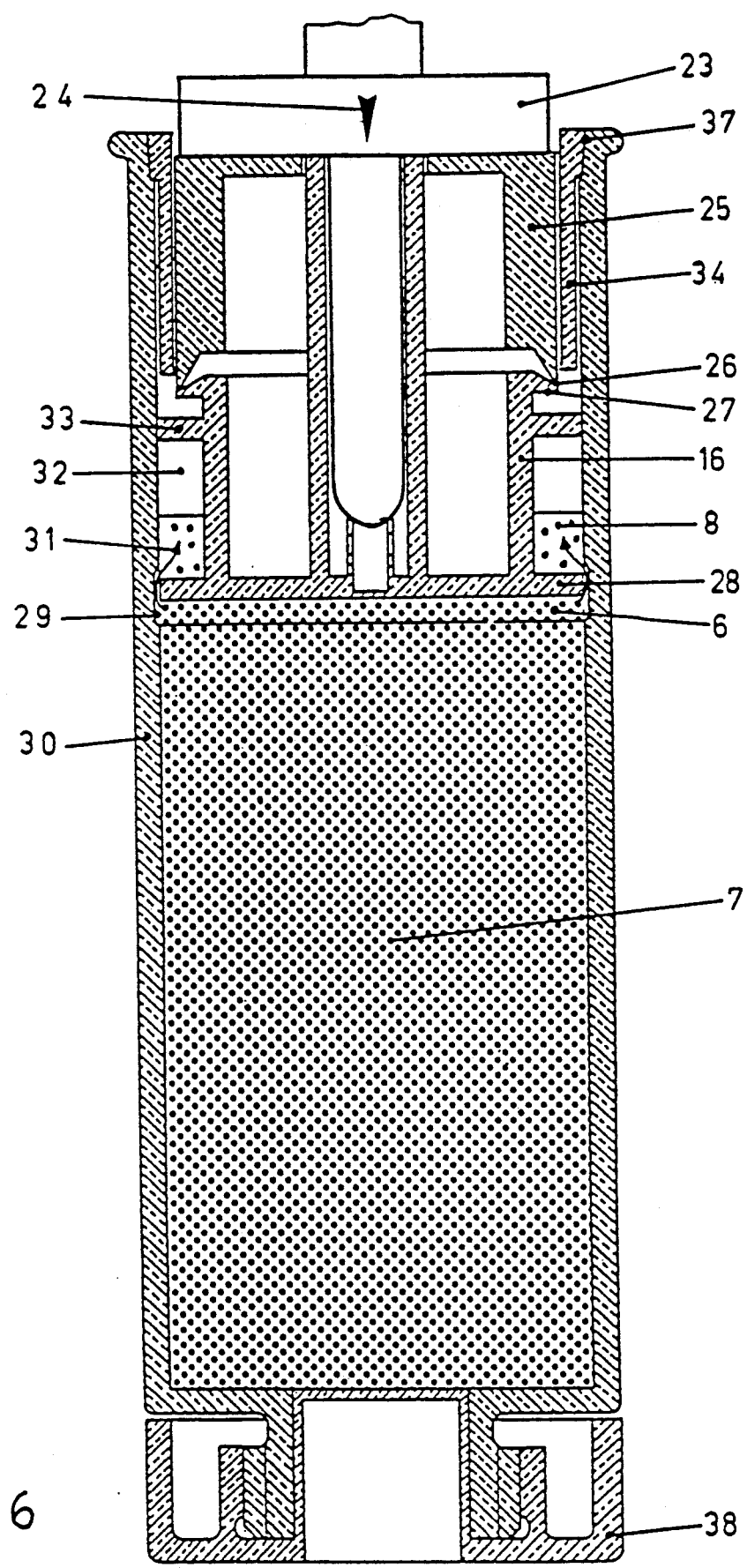
FIG. 6 is a sectional view of the syringe according to FIGS. 4 and 5 with the piston being advanced for extrusion of the cement mixture.

The flooding front as represented by arrows 22 in FIG. 5 propagates through the powder column from the back region 5 to the front region 6.

After completion of the flooding process which takes approximately 30 seconds, said adapter 13 is removed and disposed. The syringe 11 is then inserted into a caulking gun (not shown in the drawings) and the pusher 23 of the caulking gun is advanced as shown by arrow 24 in FIG. 6.

The cutting edge 26 of the cutting insert 25 of the piston 16 cuts across the annular section 27 of the piston 16. The front seal 28 of said piston 16 advances past the gap 29 in the barrel 30. The surplus liquid 8 escapes as shown by the arrow 31 in FIG. 6 into the trap 32 between the front seal 28 and the rear seal 33. The rear section 34 of said piston 16 remains fixed to the barrel 30 at the seal 37.

When the cement mixture 7 is ready for extrusion the cap 38 of said syringe 11 is removed and said cement mixture 7 is extruded.

After passing the gap 29 said front seal 28 again seals against said barrel 30 assuring full extrusion of said cement mixture 7.

In a preferred embodiment, the particles (1) or particles of any additive are of such a size and/or form that migration thereof through the interspaces is prevented.

In another preferred embodiment, the weight ratio of the powder/liquid is between about 3.6 and 2.4, preferably about 3.6 and 3.0.

Also, in an additional preferred embodiment, the evacuated interspaces between the powder particles comprise 25 to 35% of the total volume of the powder, preferably between 26 and 30% of the total volume of the powder.

What is claimed is:

1. The method of preparing a self-curing two-component powder liquid bone cement comprising a powder component consisting of particles (1) containing a polymerization catalyst (2), and a liquid component (3) containing a polymerizable monomer, prepolymer or mixtures thereof, characterized by the following steps:
   A) filling an evacuated, inflexible chamber (4) essentially completely with the particles (1) of the powder component such that the interspaces between the particles are substantially evacuated, the particles (1) consisting of a material soluble in the liquid component (3) and containing the polymerization catalyst (2) distributed throughout the particles (1);
   B) by the action of the vacuum in the interspaces between the same powder particles (1), flooding the interspaces essentially completely and wetting the powder particles completely by the liquid component (3) so that at least a surface layer (9) of said particles (1) is dissolved and the corresponding polymerization catalyst (2) contained in a portion of the particles initiates the polymerization process in the flooded cement mixture (7);
   wherein steps A) and B) are conducted under conditions wherein said powder component is tightly confined by the walls of said chamber while at the same time maintaining interspaces between the particles in an evacuated condition.

2. Method according to claim 1 characterized in that the flooded cement mixture (7), is drained from the surplus liquid component (8) by applying pressure to the cement mixture (7) and providing means for the preferential escape of the surplus liquid component (8) from the chamber (4) said means for preferential escape being such that the particles cannot escape by said means.

3. Method according to claim 2, characterized in that at least the outermost layer of said surface (9) of the said particles (1) contains less polymerization catalyst (2) than the interior regions (10) of the particles (1) and that the surface (9) of the particles (1) is preferably smooth.

4. Method according to claim 3, characterized in that the said particles (1) or particles of any additive are of such a size and/or form that migration thereof through the interspaces is prevented.

5. Method according to claim 4, characterized in that the weight ratio of the powder/liquid is between 3.6 and 2.4.

6. Method according to claim 5, characterized in that the said steps A and B are carried out in an elongated container, preferably in form of a syringe (11), containing the said evacuated powder component, by introducing the said liquid component (3) through a diaphragm (19).

7. Method according to claim 6, characterized in that the evacuated interspaces between the powder particles comprise 25 to 35% of the total volume of the powder.

8. A method of claim 3 wherein the outermost surface layer of the particles contains essentially no polymerization catalyst.

9. A method of claim 5 wherein the weight ratio of the powder/liquid is between about 3.6 and 3.0.

10. A method of claim 7 wherein the evacuated interspaces between the powder particles comprise about 26% to about 30% of the total volume of the powder.

11. The method of preparing a self-curing two-component powder liquid bone cement comprising a powder component consisting of particles comprising polymethylmethacrylate and containing a polymerization catalyst comprising benzoylperoxide, and a liquid component containing a polymerizable liquid methylmethacrylate monomer, prepolymer or mixtures thereof, characterized by the following steps:
   (a) filling an evacuated, inflexible chamber essentially completely with the particles of the powder component such that the interspaces between the particles are substantially evacuated, the particles consisting of a material soluble in the liquid component and containing the polymerization catalyst distributed throughout the particles;
   (b) by the action of the vacuum in the interspaces between the powder particles, essentially completely flooding the interspaces and completely wetting the powder particles by the liquid component and thereby at least a surface layer of said particles is dissolved and the corresponding polymerization catalyst contained in a portion of the particles initiates the polymerization process in the flooded cement mixture.

* * * * *